US00PP35461P2

(12) United States Plant Patent
Hansen

(10) Patent No.: US PP35,461 P2
(45) Date of Patent: Nov. 7, 2023

(54) ***ASTILBE* PLANT NAMED 'DARK SIDE OF THE MOON'**

(50) Latin Name: ***Astilbe* hybrid**
Varietal Denomination: Dark Side of the Moon

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 1 day.

(21) Appl. No.: 17/803,687

(22) Filed: Oct. 13, 2022

(51) Int. Cl.
*A01H 5/02* (2018.01)
*A01H 6/80* (2018.01)

(52) U.S. Cl.
USPC ..... Plt./407

(58) Field of Classification Search
USPC ..... Plt./407
CPC ... A01H 5/02; A01H 5/12; A01H 5/00; A01H 6/80
See application file for complete search history.

(56) References Cited

PUBLICATIONS

Proven Winners Perennials 2021-2022, retrieved on Mar. 30, 2023 at https://www.provenwinners.com/sites/provenwinners.com/files/catalogs_pdfs/2021-2022_new_proven_winners_perennials.pdf, 2 pp. (Year: 2022).*

The Home Depot, retrieved on Mar. 30, 2023 at https://www.homedepot.com/p/PROVEN-WINNERS-1-Gal-Dark-Side-of-the-Moon-Astilbe-Live-Plant-Black-Foliage-and-Purple-Flowers-ASLPWP1006102/320066344, 3 pp. (Year: 2023).*

* cited by examiner

*Primary Examiner* — June Hwu

(57) ABSTRACT

The new and distinct hybrid of *Astilbe* plant named 'Dark Side of the Moon' has broadly-mounded habit producing a dense bushy appearance of rich, dark chocolate-purplish, triternate foliage that is topped with tall, upright, stiff dark-mahogany-color panicles of numerous, densely-clustered, deep mauve-colored flower buds opening to densely-clustered rosy-purple flowers on heavily-branched stems. The new plant is vigorous, shows heat and sun tolerance, and is useful in the landscape, in containers, or as a cut flower.

3 Drawing Sheets

Botanical denomination: *Astilbe* hybrid.
Variety denomination: 'Dark Side of the Moon'.

STATEMENT REGARDING PRIOR DISCLOSURES UNDER 37 CFR 1.77(b)(6)

The earliest description of *Astilbe* 'Dark Side of the Moon' was in a non-enabling brief description and photograph on a website maintained by Walters Gardens, Inc. on Dec. 1, 2021. The new plant was subsequently listed in the "Walters Gardens 2022-2023 Catalog" originally sent to the public on Jun. 8, 2022, with a brief non-enabling description and photograph. The first sale of the new plant was by Walters Gardens, Inc. to W.W. Greenhouses on Jan. 1, 2022. Walters Gardens, Inc. obtained the new plant and information about the new plant directly from the inventor. No plants of *Astilbe* 'Dark Side of the Moon' have been sold, in this country or anywhere in the world, nor has any disclosure of the new plant been made, more than one year prior the filing date of this application, and such sale or disclosure within one year was either derived directly or indirectly from the inventor and as such would be a 35 U.S.C. § 102(b) exception.

BACKGROUND OF THE INVENTION

The present invention relates to a new and distinct cultivar of *Astilbe* in the Saxifragaceae family and given the cultivar name of 'Dark Side of the Moon'. 'Dark Side of the Moon' was hybridized by the inventor on Jul. 10, 2014, in the greenhouses of a wholesale perennial nursery in Zeeland, Michigan, USA and assigned the breeder code 14-6-1. The seed or female parent was *Astilbe thunbergia* 'Chocolate Shogun' U.S. Plant Pat. No. 26,430 and the male parent was 'Purpurkerze' (not patented).

*Astilbe* 'Dark Side of the Moon' was first selected in the fall of 2016 and passed final evaluation in the fall of 2017 from among several other seedlings from the same cross and other crosses. 'Dark Side of the Moon' has been asexually propagated by initially in 2018 by division of the crown at the same nursery in Zeeland, MI followed by sterile shoot tip tissue culture propagation, and the resultant plants of both propagation systems have remained stable and continued to exhibit the same characteristics as the original plant for multiple generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype. The following traits in combination have been repeatedly observed and are determined to be the unique characteristics of 'Dark Side of the Moon' and distinguish the new cultivar as a new and distinct *Astilbe* plant:

1. Broadly upright and mounding plant habit;
2. Vigorous growth habit;
3. Dense and bushy appearance;
4. Emerging leaves are chartreuse with a moderate burgundy blush and a burgundy rim, developing into rich, dark chocolate-purplish foliage;
6. Tall, upright, dark-mahogany-colored panicles;
7. Numerous, densely-clustered, deep mauve-colored flower buds that open to densely-clustered rosy-purple flowers on tall heavily-branched stems;
8. Good garden performance.

The nearest comparison *Astilbe* plants known to the inventor besides the parents include: 'Chocolate Cherry' U.S. Plant Pat. No. 27,676, *A. chinensis* 'Visions' (not patented), *A. chinensis* 'Maggie Daley' (not patented), and 'Amber Moon' U.S. Plant Pat. No. 26,028.

'Chocolate Cherry' has dark green foliage with burgundy overtones and the flowers are more airy and reddish colored. 'Visions' has medium green foliage with raspberry-pink flowers. 'Maggie Daley' has dark green foliage and bright lavender-purple flowers. 'Amber Moon' has foliage that is chartreuse tinged reddish in the spring, and the flowers are rosy-pink.

The male parent, 'Purpurkerze', has flowers of rich violet-red that lighten to light purple as they age, and the foliage is dark green. The female parent, 'Chocolate Shogun', has dark purplish-brown foliage and the flowers are pale pinkish-white and the inflorescence is denser.

BRIEF DESCRIPTION OF THE DRAWINGS

The photographs of the new plant demonstrate the overall appearance of *Astilbe* 'Dark Side of the Moon' including the unique traits. The colors are as accurate as reasonably possible with modern color reproductions. Some slight variation of color may occur as a result of lighting quality, intensity, wavelength, and direction or reflection. The photographs are of a three-year-old plant grown in a partially shaded display garden.

DETAILED BOTANICAL DESCRIPTION

Figure 1:
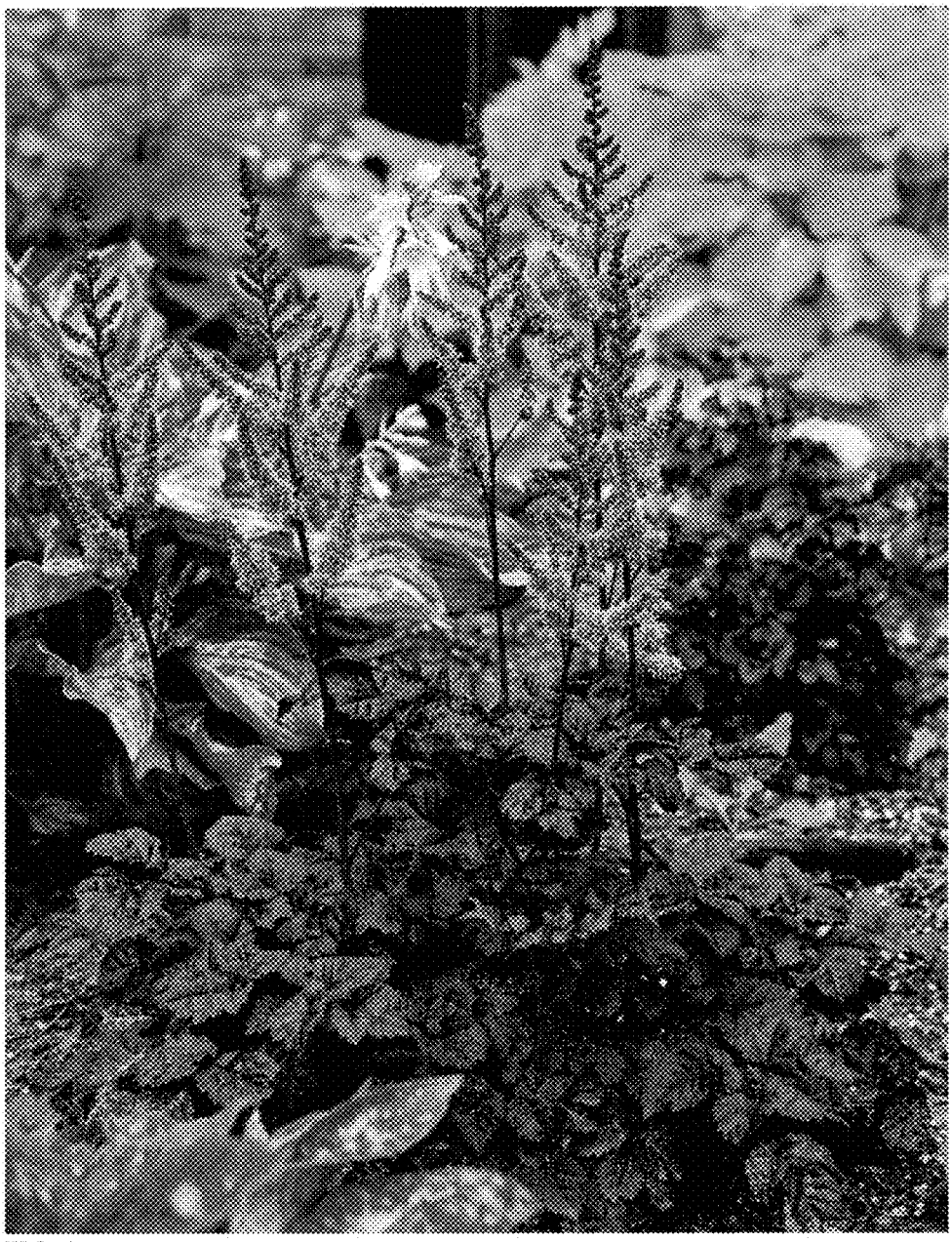
FIG. 1 shows a plant in peak flowering season.
Figure 2:
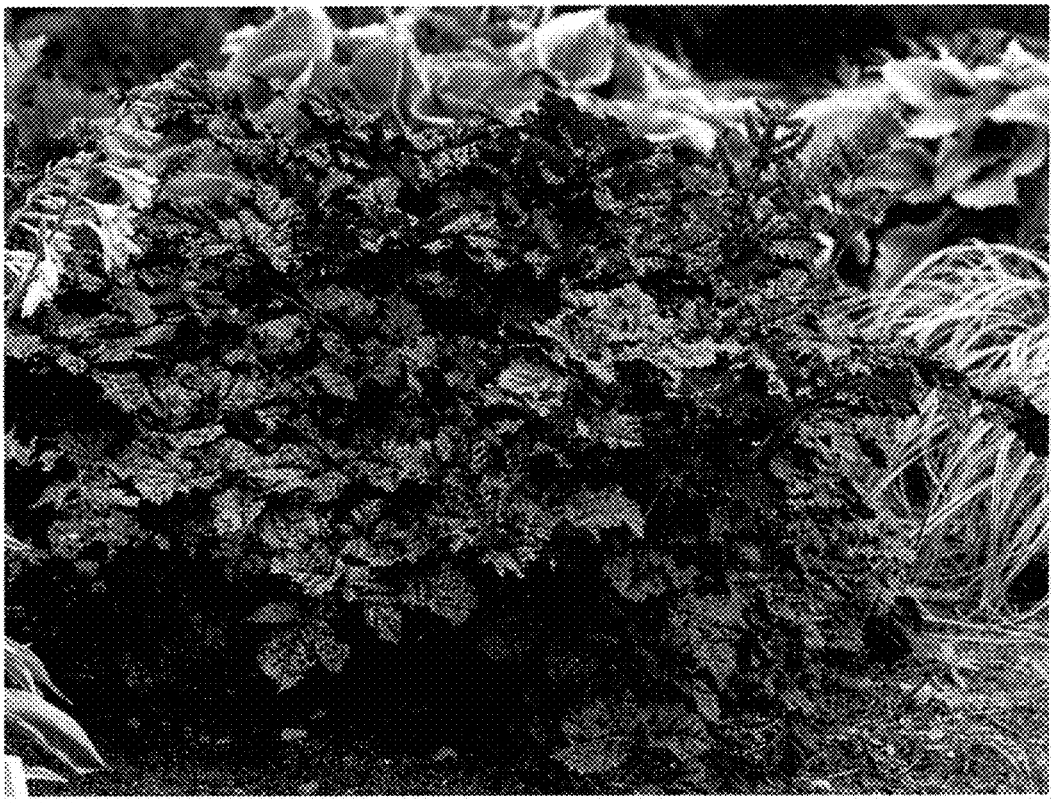
FIG. 2 shows the foliage of a plant prior to flowering.
Figure 3:
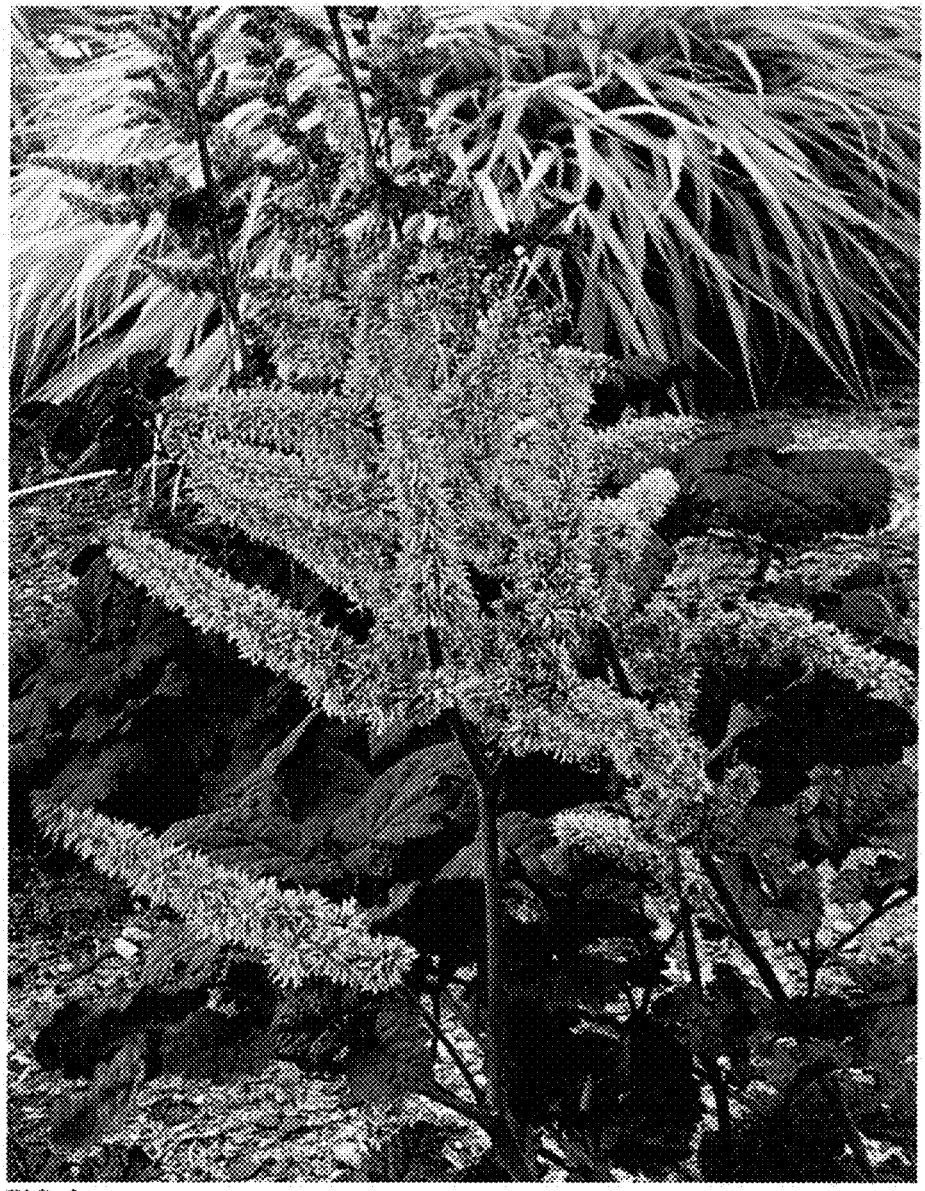
FIG. 3 shows a close-up of the flowering stem.

The following description is based on three-year-old plants growing in a lightly shaded greenhouse, partially-shaded outdoor display gardens, or full-sun display gardens in Zeeland, Michigan, USA. The new plant has not been grown under all possible environments and may phenotypically appear different under different conditions such as light, temperatures, fertilizer, and water, without any difference in genotype. The color descriptions used are from the 2015 edition of The Royal Horticultural Society Colour Chart except where common dictionary terms are used.

Botanical classification: *Astilbe* hybrid;

Parentage: Female or seed parent *Astilbe thunbergia* 'Chocolate Shogun' and the male or pollen parent *Astilbe chinensis* 'Purpurkeze';

Propagation: By crown division and shoot tip tissue culture;

Time to initiate roots: About three weeks at temperatures about 20° C.;

Root description: Freely-branching; dense; becoming thick, fleshy; color of the roots is dependent on age, substrate composition, water quality, fertilizer type, and formulation; color typically young roots NN155B, older roots nearest RHS 166B;

Plant habit: Herbaceous winter-hardy perennial; broadly mounding plant form with inflorescences held well above the foliar plane; flowering stems and leaves basal;

Growth rate: Moderately rapid to rapid; from 25 cm plug finishing in about three months to produce fully-grown flowering plants in 3.8-liter pot;

Plant size: Foliage to about 37 cm tall and 82 cm wide; panicle to about 106 cm tall and about 17 cm wide;

Stem description: About 107 cm long and 6 mm diameter at base; erect; strong; stiff; puberulent;

Internode length: About 7 cm;

Stem color: Nearest RHS N186C distally and transitioning to nearest RHS 146D proximally;

Leaf description: Alternate; triternate, leaflets three with three leaflet sections on each; crinkled, not flat; foliate portion to 35 cm long and 26 cm wide; main side leaflet to 17.5 cm wide and 17.5 cm long; main terminal leaflet to 23 cm wide and 20 cm long; terminal sub-leaflets to 14.5 cm wide and 13 cm long; sub-leaflet shape ovate to cordate; rarely lobed; apex acute, base truncate to cordate, margin irregularly to compound crenate and finely apiculate; adaxial surface lustrous, sparsely setulose; abaxial surface glabrous, matte;

Leaflet color: Developing adaxial nearest RHS NN137C with moderate blush of nearest RHS 187A in center intensifying along margin to solid RHS 187A, developing abaxial between RHS 187A and RHS N186C; mature adaxial between RHS N187A and RHS 187A, mature abaxial between RHS 147B and RHS N138B;

Leaflet venation: Pinnate; adaxial furrowed, sparsely setulose, and lustrous becoming matte with age; abaxial costate, matte, and sparsely setulose;

Leaflet vein color: Adaxial expanding nearest RHS 185C, abaxial expanding midrib nearest RHS 187C and secondary veins proximally nearest RHS 185B and distally becoming nearest RHS 185D; adaxial mature between RHS 187A and RHS N187A, abaxial mature midribs between RHS 185B and RHS 185C, secondary veins proximally nearest RHS 185C, and distally nearest RHS 197C;

Petiole: Cylindrical with single furrow; sparsely setulose and matte; base swollen and clasping; to 30 cm long from base to swollen rachis node and 6 mm diameter above swollen base; distal node swollen to 12 mm across and 9 mm tall; base swollen to about 13 mm tall and 14 mm wide;

Petiole and node color: Variable, adaxial between RHS 187A and RHS 187B in high light and abaxial in low light or shaded between RHS 182D and RHS 196C; base nearest RHS 187B;

Rachis: Cylindrical with single furrow; sparsely setulose; two side rachis to about 78 mm long to initial branch and 2.5 mm diameter at base, terminal rachis to about 125 mm long to initial branch and 3.5 mm diameter near middle;

Fragrance: Faint, lightly sweet;

Flowering season: Begin flowering early summer; inflorescence effective for about 10 to 14 days on the plant or as cut flower;

Flower quantity: About 4,000-5,000 flowers per inflorescence;

Flower buds one to two days prior to opening: Ellipsoidal to globose; rounded base, acute apex; glabrous, smooth, matte; to about 2.5 mm long and 2.0 mm diameter;

Flower bud color: Calyx nearest RHS N79C with exserted petals nearest RHS N82B;

Inflorescence: Panicle; to about 106 cm tall, flowering in upper 37 cm and to about 12 cm wide;

Flower: Perfect; complete; rotate; to about 10 mm across and 6 mm tall;

Petals: Typically, five in a single whorl; oblanceolate; apex rounded; base cuneate; margin entire; glabrous; slightly lustrous; to about 6 mm long and 0.7 mm wide near apex;

Petal color: Adaxial and abaxial between RHS N82C and RHS N82D; no change in color with development;

Calyx: Campanulate; about 3 mm long and 2.5 min across at apex;

Sepals: Typically, five; lanceolate; about 2 mm long and 1 mm across; apex: acute; basal one-third fused; margin entire; adaxial and abaxial glabrous and lustrous;

Sepal color: Adaxial and abaxial nearest RHS 71A; color does not change with development;

Androecium: Typically, ten;

*Filament*.—Cylindrical; straight; about 4.5 mm long and 0.1 mm diameter; color proximally nearest RHS 77A, distally becoming nearest RHS 76D.

*Anther*.—Oblong to ellipsoidal; basifixed; longitudinal; to about 1 mm long and 0.5 mm across; color prior to dehiscing nearest RHS NN155B.

*Pollen*.—Scarce; color nearest RHS 196C.

Gynoecium: Typically, two per flower; about 4 mm long;

*Stigma*.—Minute, globose; about 0.2 mm across; color nearest N155D.

*Style*.—Bifid; to about 2 mm long and 1 mm across at base; color between RHS 71A and RHS 71B proximally and nearest RHS 69D below stigma.

*Ovary*.—Globose; to about 0.5 mm diameter; color nearest RHS N155D.

Peduncles: Cylindrical; puberulent; matte; to about 106 cm tall and about 6 mm diameter at base; stiff; strong; erect;

Peduncle color: Nearest RHS N186C in flowering portion;

Pedicels: Short or absent; cylindrical; about 0.5 mm. diameter and to about 0.2 mm long;

Pedicel color: Too small to obtain color description when present;

Seeds and fruits: No seed and fruit development have been observed;

Disease and pest resistance: 'Dark Side of the Moon' has not been noted to be resistant to pathogens and pests common to *Astilbe;*

Garden performance: Plants of the new *Astilbe* have been observed to have good garden performance, tolerate strong wind and rain, and are more heat and sunlight tolerant than typical *Astilbe*. The new plant is suitable for at least USDA Hardiness Zones 4 through 9.

It is claimed:

1. The new and distinct *Astilbe* plant named 'Dark Side of the Moon' as herein described and illustrated.

* * * * *